United States Patent
Johnson

[11] Patent Number: 5,928,240
[45] Date of Patent: *Jul. 27, 1999

[54] APPARATUS FOR FORMING A CENTERED BORE FOR THE FEMORAL STEM OF A HIP PROSTHESIS

[76] Inventor: Lanny L. Johnson, 2950 E. Mount Hope Rd., Okemos, Mich. 48864

[*] Notice: This patent is subject to a terminal disclaimer.

[21] Appl. No.: 09/118,854

[22] Filed: Jul. 20, 1998

Related U.S. Application Data

[63] Continuation-in-part of application No. 08/840,548, Apr. 3, 1997, which is a continuation of application No. 08/389,399, Feb. 16, 1995, abandoned.

[51] Int. Cl.⁶ .................................................. A61B 17/56
[52] U.S. Cl. .............................. 606/79; 606/86; 606/102
[58] Field of Search ................................ 606/86, 92, 93, 606/94, 95, 85, 80, 79, 102

[56] References Cited

U.S. PATENT DOCUMENTS

| | | |
|---|---|---|
| 4,337,773 | 7/1982 | Raftopoulos et al. . |
| 5,013,318 | 5/1991 | Spranza, III . |
| 5,108,405 | 4/1992 | Mikhail et al. . |
| 5,122,134 | 6/1992 | Borzone et al. ........................ 606/80 |
| 5,171,248 | 12/1992 | Ellis ...................................... 606/102 |
| 5,190,548 | 3/1993 | Davis ..................................... 606/80 |
| 5,470,336 | 11/1995 | Ling et al. . |

*Primary Examiner*—Guy V. Tucker
*Attorney, Agent, or Firm*—Pillsbury Madison & Sutro LLP

[57] ABSTRACT

Apparatus for forming a centered bore within an intramedullary canal of a femur in preparation for the implantation of a prosthetic device is disclosed. The apparatus comprises an elongated rigid rod having a handle adjacent its proximal end. The rod includes outwardly projecting fins at its distal end adapted to engage the interior wall of the cortex of the femur, thus centering the bore. Additionally, the rod has a hollow interior which permit suction to be applied to rod's proximal end.

4 Claims, 5 Drawing Sheets

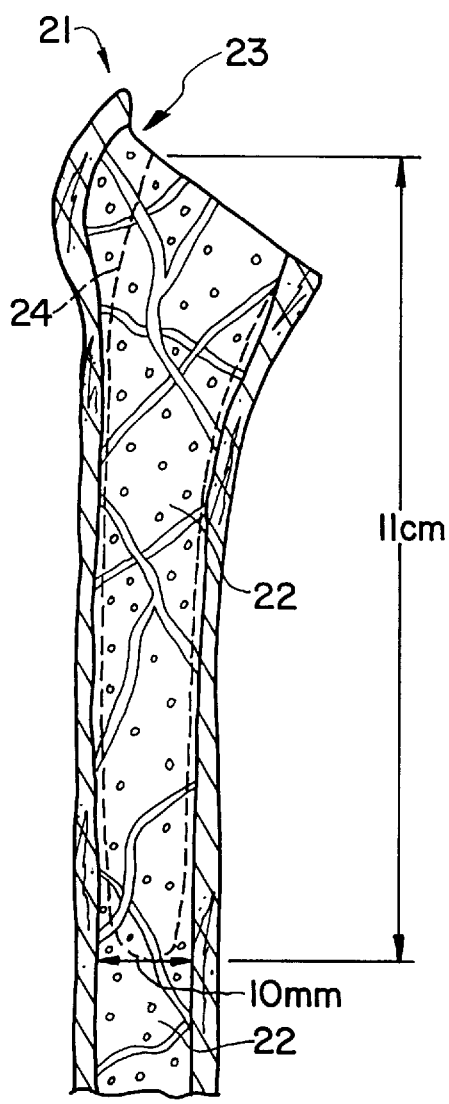
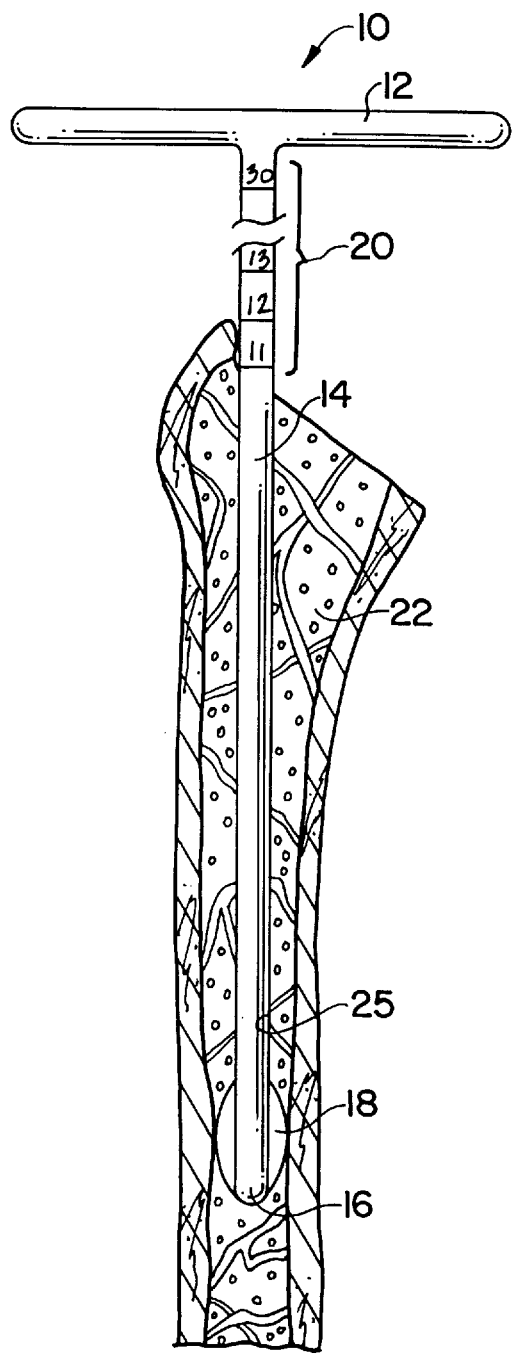
FIG. 2                     FIG. 3

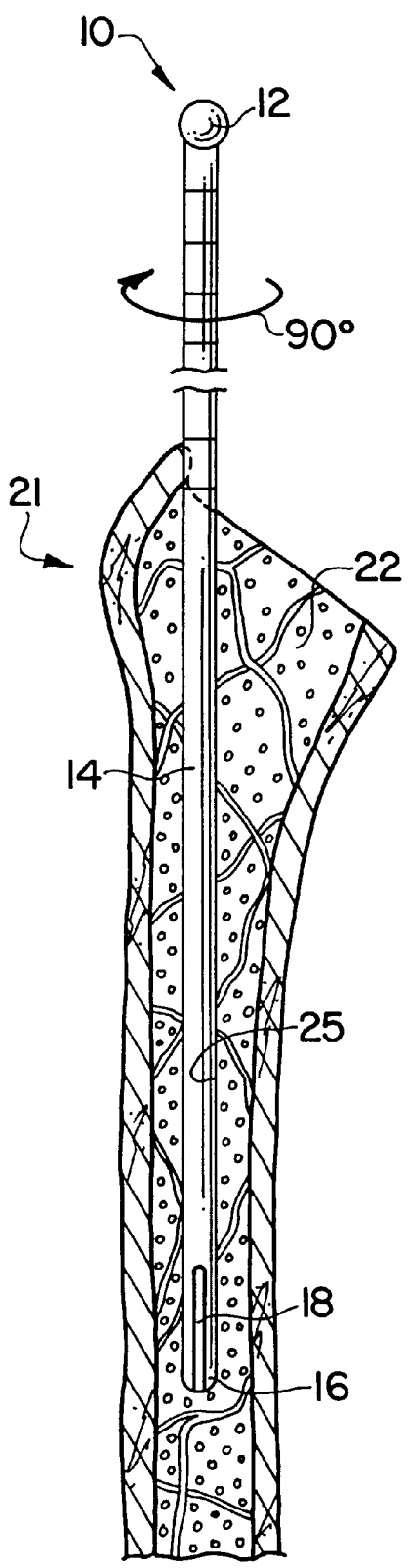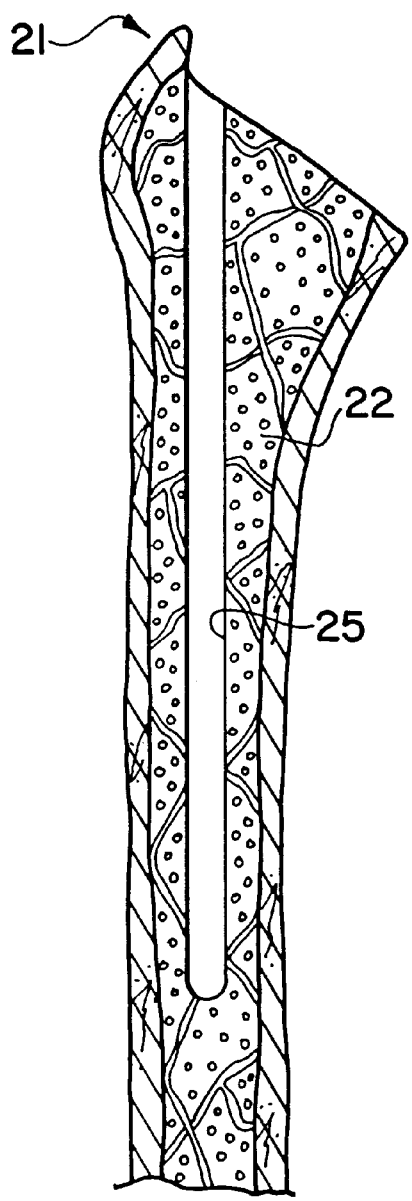
FIG. 4
FIG. 5

5,928,240

APPARATUS FOR FORMING A CENTERED BORE FOR THE FEMORAL STEM OF A HIP PROSTHESIS

This application is a continuation-in-part of Application No. 08/840,548, filed Apr. 3, 1997, still pending which is a continuation of Application No. 08/389,399 filed Feb. 16, 1995, now abandoned.

BACKGROUND OF THE INVENTION

1. Field of the Invention

The present invention relates to the implantation of prosthesis devices, and, more particularly, to the preparation of the femur for the implantation of a prosthetic hip replacement device therein by the formation of a centered bore in the intramedullary canal of the femur.

2. Related Art

Bone diseases and injuries to joints often make it necessary or desirable to replace a natural joint with an artificial prosthesis. One such replacement involves the fixation of a stem of a prosthetic hip joint within the femur. The femur contains an intramedullary canal filled with cancellous bone within which the stem of the prosthesis can be implanted. With such implantation, it is desirable to fix the stem to the femur centrally within the intramedullary canal.

In preparing the femur to accept the prosthetic device, the femoral head is removed to expose the intramedullary canal. A bore is formed in the canal and the femoral stem of the prosthesis is inserted into the canal and fixed to the femur by an interference fit, or by cement fixation.

When the prosthesis is joined with the femur, it is ideally centered within the intramedullary canal so that there is no undue pressure on the cortical bone which might cause pain to the recipient of the prosthesis and even result in bone penetration. The centering of the femoral stem of a prosthesis has been addressed. For example, Techmedia, a company located in Camarillo, Calif., has proposed using a small plastic centering device attached to the tip of the femoral stem. However, the attachment of such a device to a femoral stem creates several associated problems. For example, such plastic attachments increase the overall cost of the prosthesis. Additionally, the attachment of a plastic centering device to a metal femoral stem often causes some weakening of the stem, thus increasing the chance of deterioration of the fixation of the prosthesis to the femur and the likelihood that the prosthesis will need replacement. High intramedullary pressure may cause septic fat embolism, i.e., cardiac arrhythmia, death.

SUMMARY OF THE INVENTION

An object of the present invention is to overcome the problems noted above. The invention centers the femoral stem of a prosthesis within the intramedullary canal in a patient's femur so that no undue pressure is placed on the cortical bone which could cause pain to the patient and even result in cortical bone penetration.

According to the present invention, a device for preparing the femur for prosthesis implant is formed in assorted sizes so as to fit the intramedullary canal of any patient. The device is inserted into the intramedullary canal. The device includes an elongated rod having fins joined to the rod's distal end, the fins projecting outwardly from the rod and being disposed at 180° to one another relative to the rod. As the device is inserted into the canal, it first is oriented with the fins extending in an anterior-posterior relationship to the femur, and with the fins engaging the cortical bone, whereby the device creates a bore which is centered, front to back, relative to intramedullary canal. The device is then removed, rotated ninety degrees, and reinserted in the bore, thus centering the device in its medial to lateral relationship with the femur. The bore that is thus formed is centered at a depth established by length of rod inserted into the intramedullary canal. When the femoral stem of the prosthesis subsequently is implanted within the bore, it is properly positioned.

A further object of the invention is to utilize a hollow elongated rod having an open distal end, and/or openings in the wall of the rod adjacent the distal end, to permit suction to be applied at the rod's proximal end so that marrow can be withdrawn as the device is inserted into the intramedullary canal. This decompresses the bore formed by the device and decreases the chance that marrow tissue will be forced into the blood when a broach or prosthesis is inserted within the bore.

In accordance with a further object of the invention, a method is provided for forming a cavity in a femur for receiving a prosthetic device. As a preliminary step, the femoral head is removed so as to expose the femur's intramedullary canal. The method then includes the step of selecting a device of the type described above that will fit within the intramedullary canal such that its fins will engage the cortical bone of the patient. The device is then inserted, withdrawn and reinserted into the intramedullary canal in the manner previously discussed so as to create a bore which is centrally positioned relative to the femur's cortical bone. Once the bore is so formed, the femoral stem of the prosthetic device may be attached to the bone in a manner so that the prosthesis is centered with respect to the bone. Typically, the bore will require enlargement prior to attachment of the prosthesis. This may be done by compacting the walls of the bore using a device such as that disclosed, for example, in U.S. patent application Ser. No. 08/309,592, entitled "Instrument for Proximal Femoral Compaction Broaching", the subject matter of which is incorporated herein by reference.

Other objects, features and characteristics of the present invention, as well as the function of the related elements of the structure, and the economies of manufacture, will become more apparent upon consideration of the following detailed description and the appended claims, with reference to the accompanying drawings, all of which form a part of this specification.

BRIEF DESCRIPTION OF THE DRAWINGS

FIG. 2 is a cross-sectional view of a portion of a femur in which a prosthetic device is to be fit;

FIGS. 3 and 4 illustrate a process of forming a bore within the intramedullary canal of the femur shown in FIG. 2;

FIG. 5 depicts the bore formed by the process illustrated in FIGS. 3 and 4;

DETAILED DESCRIPTION OF THE PRESENTLY PREFERRED EXEMPLARY EMBODIMENT

Figures 1A, 1B:
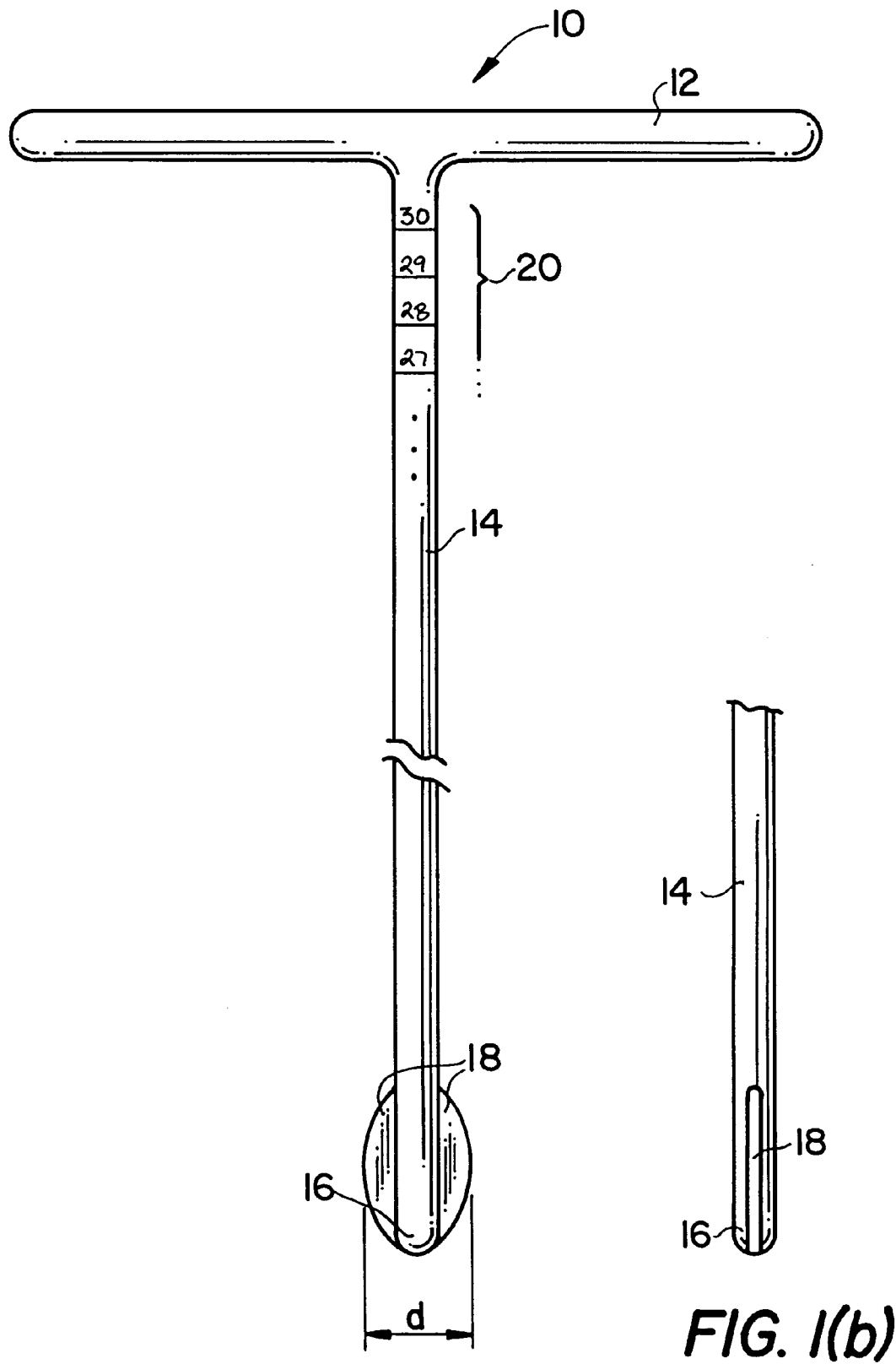
FIGS. 1(a) and 1(b) are, respectively, segmented front and side elevational views of a device according to the present invention.

Referring to FIGS. 1(a) and 1(b), the device used to form a bore in an intramedullary canal of a femur is generally shown at 10. The device is substantially T-shaped and includes a handle 12 joined to an elongated rod 14, preferably of circular cross section. At the distal end 16 of rod 14, fins 18 are formed. Fins 18 are substantially semi-elliptical in shape for the reason which will be described hereafter. They are positioned 180° apart and project outwardly from the rod.

The handle 12 is of sufficient length to permit the surgeon to insert the rod 14 into the intramedullary canal and withdraw it. Furthermore, the handle facilitates manipulation and orientation of device 10.

Preferably, rod 14 is at least 30 cm long, and is made of rigid metal provided with graduated markings along its length. The markings 20 permit the surgeon to determine how far rod 14 has been inserted into the intramedullary canal thereby permitting bores of different length to be formed. Fins 18 are formed integrally with rod 14 so as to avoid fracture or separation. A span d (FIG. 1(a)) encompassed by the fins is dimensioned so that the outer surfaces of the fins will engage the interior wall of cortical bone within the femur. Typically, the span will be about twelve mm. It will be understood, however, that the device 10 will be produced in assorted sizes, for example, with spans varying about one or two mm between sizes, so as to accommodate use within femurs of different dimensions. Ideally, device 10 will be available in ten to twenty different sizes in a set of instruments.

As can be appreciated from FIG. 1(b), fins 18 have planar surfaces which typically are between one and two mm apart. This is substantially less than the diameter of rod 14, which nominally has a five mm diameter.

FIG. 2 illustrates an end of a femur, shown generally at 21, to which a prosthetic device is to be attached. The first step in preparing femur 21 for implantation of the femoral stem of a prosthetic device is to expose the femur's proximal neck 23 and intramedullary canal 22 by removal of the femoral head. Cancellous bone is contained within the intramedullary canal. The anticipated position of a femoral stem within such bone is denoted by dotted line 24.

In practice, utilizing a procedure such as x-ray, preliminary measurements are made of a patient's intramedullary canal diameter at a depth appropriate for implantation of the femoral stem. For the sake of example, FIG. 2 shows a measurement wherein the depth of the anticipated femoral stem is eleven cm, and the width of canal 22 is ten mm at that depth. These measurements inform the surgeon as to the size of device 10 which is required.

The surgeon selects a device 10 having a ten mm span d. The rod 14 is then inserted into canal 22, as shown in FIG. 3, until the graduated markings 20 show that it is eleven cm deep. As the rod is inserted, the fins 18 are oriented in the anterior-posterior plane of the femur. As the fins 18 approach the preestablished depth of eleven cm, they engage the interior wall of the femur's cortical bone. This causes the rod 14 to be centered within the intramedullary canal. Rod 14 is then withdrawn. In this manner, rod 14 forms a bore 25 having compacted cancellous bone material along its wall and at the bottom of the bore. Because of the rod's anterior-posterior orientation during insertion, the bore is centered front to back within the intramedullary canal. If the selected rod 14 is unable to reach the desired depth, i.e., eleven cm, a smaller device 10 is chosen to form the bore.

FIG. 4 illustrates the next step in the process. After rod 14 is removed from bore 25, the device is rotated ninety degrees and rod 14 is reinserted into bore 25 with fins 14 in medial to lateral orientation relative to the femur. Rod 14 again is displaced until it reaches the eleven cm marking 20. At that point fins 18 engage the cortical bone so that the rod again is centered within the intramedullary canal.

The bore 25 created by the above-described process is shown in FIG. 5. It is eleven cm deep and is centered within intramedullary canal 22. Because of the fins' semi-elliptical shape, the rod 14 can be smoothly inserted and withdrawn from the femur.

As an alternative to the two-step insertion process just described, four fins 18, spaced at 90° intervals about rod 14, can be employed so that a centered bore is created by a single insertion and withdrawal of the rod.

Figure 6:
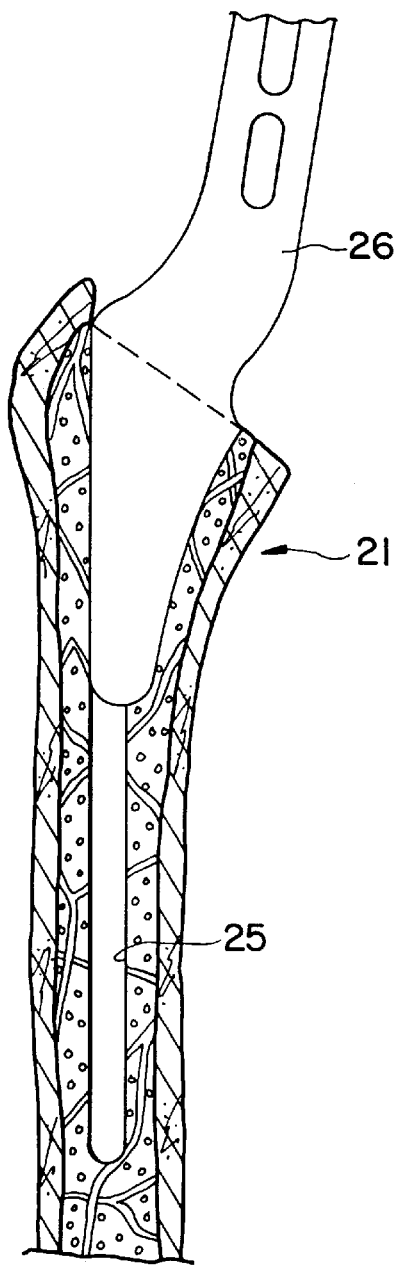
FIG. 6 shows the insertion of a first serial compactor into the bore for shaping the femur to receive the prosthetic device.

FIG. 6 illustrates the use of a compacting device 26 to widen and shape bore 25 at the proximal end of femur 21. Compacting device 26 is a broach having the general configuration of the upper portion of the femoral stem of the prosthesis being implanted. As described in detail in the above-referenced Application Ser. No. 08/309,592, the broach further compacts the cancellous bone material found along the wall of bore 25, thus providing additional side wall support for the prosthesis. Several broaches of differing sizes may be used to progressively enlarge and shape bore 25 at this location.

Figure 7:
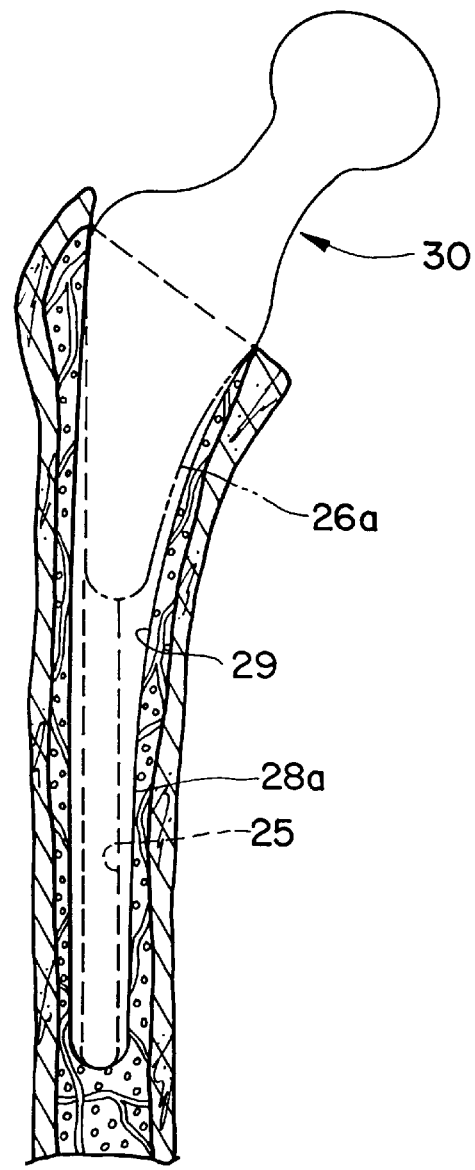
FIG. 7 illustrates the prosthetic device attached to the femur.

In FIG. 7, the bore has been enlarged to accommodate the femoral stem 29 of prosthetic device 30. Original bore 25 is shown by a dotted line. Reference number 28a illustrates the enlarged bore formed by further compacting the cancellous bone material with devices having the general shape of the femoral stem. Dotted line 26a indicates the outline of the wall formed by compactor 26 (shown in FIG. 6) once the compactor is removed. In this manner, the entire cavity is formed to receive the femoral stem. The prosthesis then can be secured to the femur by conventional cement or non-cement techniques.

If a cement restraint is desired for an implanted prosthesis and insufficient bone is available at the bottom of bore 25 for that purpose, additional bone material can be harvested from the amputated femoral head and packed down into the bottom center of the bore.

In the embodiments described, the fins 10 are formed integrally with the rod 14 from a single piece of metal stock. Alternatively, they could be detachably secured to the rod and made of metal or synthetic materials.

The handle 12 is illustrated in FIG. 1(a) as being fixed to rod 14. However, it also can be removable. In the latter case, with rod 14 inserted within the intramedullary canal and the handles removed, the rod can serve as a guideway for cannulated compactors to enlarge and shape bore 25.

Figure 8:
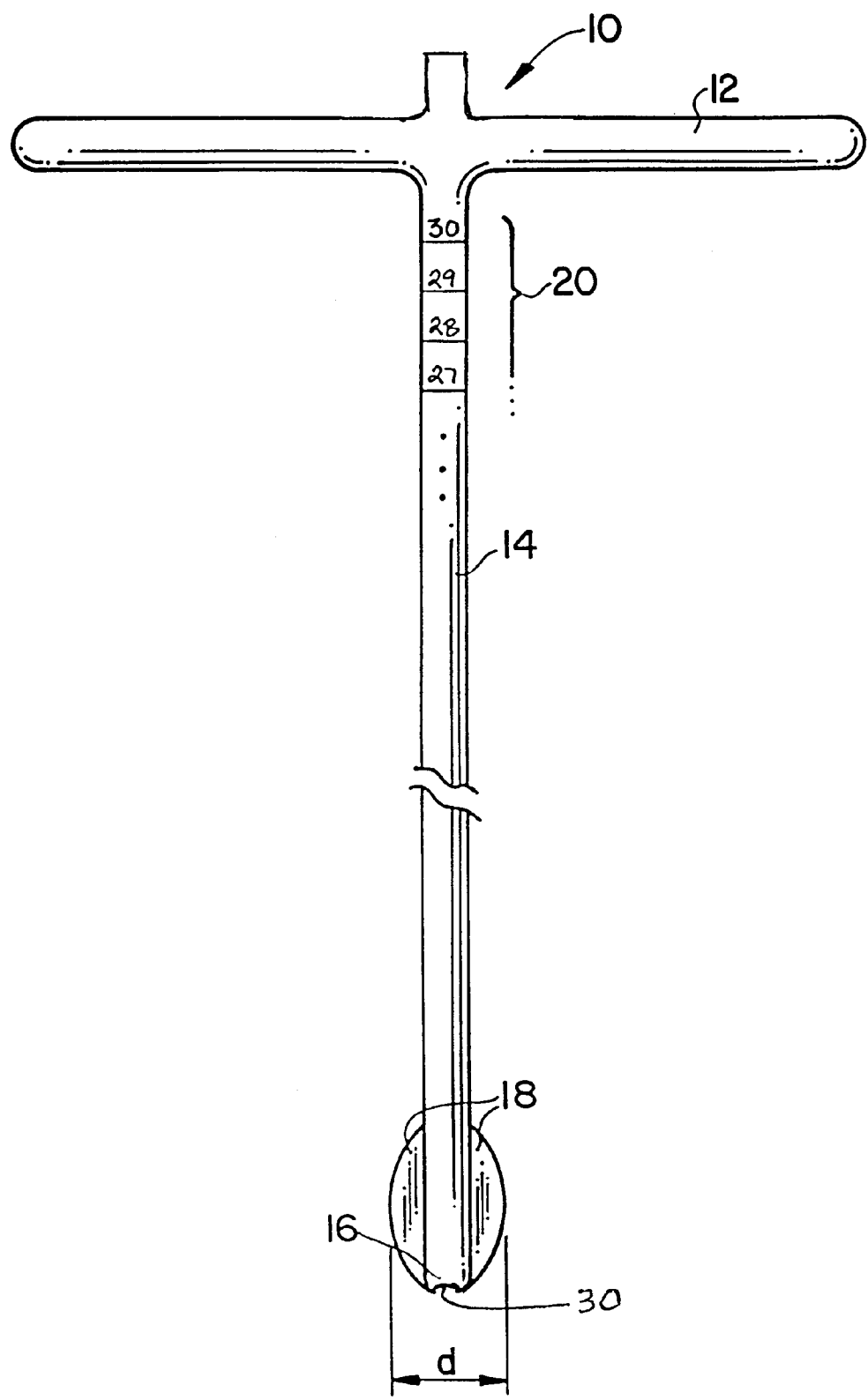
FIG. 8 is a side elevational view of an alternative embodiment of a device according to the present invention.

In an alternative embodiment illustrated in FIG. 8, the elongated rod 14 is hollow having an opening 30 at its distal end. The proximal end of the rod extends above the handle 12 and also includes an opening to which a suction source is connected. When suction is applied and the device is inserted within the intramedullary canal, marrow is withdrawn as the bore in the canal is formed. This removal of narrow decompresses the bore and decreases the chance that marrow tissue will be forced into the blood when a prosthesis is inserted with the bore.

In addition to, or in substitution for opening 30, the wall of rod 14 at its distal end may be provided with one or more openings communicating with the hollow interior of the rod.

While the invention has been described in connection with what is presently considered to be the most practical and preferred embodiments, it is to be understood that the invention is not limited to the disclosed embodiments, but, on the contrary, is intended to cover various modifications and equivalent arrangements included within the spirit and scope of the appended claims.

What is claimed is:

1. An instrument for forming a centered bore in a femur in preparation for implantation of a femoral prosthesis, wherein the femur includes an intramedullary canal defined by an interior wall of cortical bone, the instrument comprising:

an elongated rod sized to be received within said canal, said rod having a hollow interior and openings at distal and proximal ends of the rod communicating with said interior;

a handle joined to the rod adjacent the proximal end of the rod; and fins non-retractably disposed in a fixed position at the distal end of the rod and projecting outwardly from the rod, in a single planar relationship, for engaging the interior wall of the cortical bone when said rod is inserted within the canal so as to center the rod relative to the wall.

2. An instrument as set forth in claim 1, wherein each fin has an outer surface which is semi-elliptical in shape.

3. An instrument as set forth in claim 2, wherein said rod is provided with graduated markings along its length.

4. An instrument as set forth in claim 1, wherein said rod is provided with graduated markings along its length.

* * * * *